United States Patent [19]

Stammler

[11] Patent Number: 5,969,179
[45] Date of Patent: Oct. 19, 1999

[54] METHOD FOR PREPARING ENANTIOMERIC FORMS OF AMINO ALKYLAMINOPHENYL PROPANOIC ACID

[75] Inventor: Robert Stammler, Paris, France

[73] Assignee: Rhône-Poulenc Rorer S.A., Antony, France

[21] Appl. No.: 08/981,038

[22] PCT Filed: Jun. 10, 1996

[86] PCT No.: PCT/FR96/00872

§ 371 Date: Dec. 11, 1997

§ 102(e) Date: Dec. 11, 1997

[87] PCT Pub. No.: WO96/41794

PCT Pub. Date: Dec. 27, 1996

[30] Foreign Application Priority Data

Jun. 12, 1995 [FR] France .................... 95 06890

[51] Int. Cl.[6] .................................. C07C 229/40
[52] U.S. Cl. .......................................... 562/443
[58] Field of Search ............................. 562/443

[56] References Cited

U.S. PATENT DOCUMENTS 4,647,694 3/1987 Hosztafi et al. .............. 562/443

OTHER PUBLICATIONS

*Chemical Abstracts*, vol. 55, No. 22, Abstract No. 22226g (1961).
F. Bergel et al., 19. Cyto–Active Amino Acids and Peptides. Part V. Derivatives of p–Amino and p–Mercapto–phenylalanine, J. Chem. Soc. (1959), pp. 90–97. (with Chemical Abstract vol. 53, No. 13, Abstract No. 12202g (1959).

*Primary Examiner*—Brian M. Burn
*Assistant Examiner*—Brian J. Davis
*Attorney, Agent, or Firm*—Finnegan, Henderson, Farabow, Garrett & Dunner, L.L.P.

[57] ABSTRACT

A process for preparing an enantiomeric form of 2-amino-3-(4-alkylaminophenyl)-propanoic acid of formula (I) or a salt thereof:

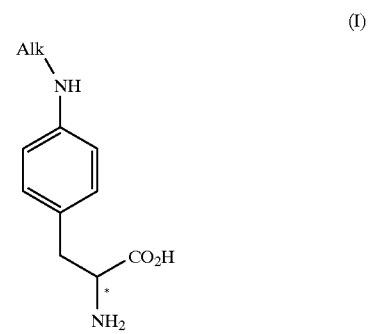

(I)

in which Alk represents an alkyl radical containing 1 to 2 carbon atoms, from (L)-phenylalanine to obtain the (S)-enantiomer of 2-amino-3-(4-alkylaminophenyl)-propanoic acid, or from (D)-phenylalanine to obtain the (R)-enantiomer of 2-amino-3-(4-alkylaminophenyl)propanoic acid.

1 Claim, No Drawings

METHOD FOR PREPARING ENANTIOMERIC FORMS OF AMINO ALKYLAMINOPHENYL PROPANOIC ACID

The present invention relates to a process for the preparation of one enantiomeric form of 2-amino-3-(4-alkylaminophenyl)propanoic acid of general formula:

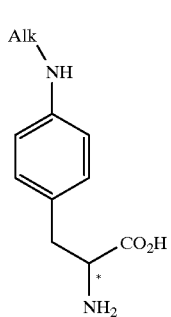

(I)

in which Alk represents an alkyl radical containing 1 to 2 carbon atoms, and salts thereof.

The preparation of (2S)-2-amino-3-(4-methylaminophenyl)propanoic acid has been described in patent application WO 94/08014, by the action of an N-methyltransferase on p-amino-(L)-phenylalanine. However, this preparation would not be exploitable industrially on account of the very low yields.

The preparation of racemic 2-amino-3-(4-methylaminophenyl)propanoic acid has been described by B. L. Moldaver and Z. V. Pushkareva, Chem. Abstr., 55, 22226g; furthermore, the specificity of this reaction does not guarantee the production of N-monomethylated compound (on synthesizing diethyl p-dimethylaminobenzyl-N-acetylaminomalonate, the presence is observed, after crystallization, of a mixture of p-aminophenylalanine and its mono- and dimethyl derivatives in the crystallization mother liquors).

It has now been found that the enantiomeric forms of this acid can be prepared directly from (L)-phenylalanine or from (D)-phenylalanine, depending on whether it is desired to obtain the (S) or (R) form of the acid respectively, in high yields and with a product of good quality.

According to the invention, (L)- or (D)-phenylalanine, whose amine function is optionally protected, is nitrated, and the nitro radical of the 4-nitrophenylalanine obtained, of general formula:

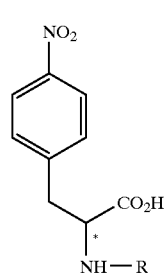

(II)

in which R is a hydrogen atom or a protecting radical, is then converted into an alkylamino radical, after protection (if R is hydrogen) of the amine function of the phenylalanine.

The nitration is carried out by nitric acid in sulphuric medium, at a temperature of between −10 and −20° C.

The protection of the amino radical is carried out according to the known methods, by a protecting radical R whose installation and removal do not affect the rest of the molecule. In particular, the process is performed according to the methods described by T. W. Greene, Protective Groups in Organic Synthesis, A. Wiley-Interscience Publication (1981), or by McOmie, Protective Groups in Organic Chemistry, Plenum Press (1973). Preferably, the amino radical is protected in the form of amide by a radical R=acyl, more particularly by an acetyl radical; or alternatively the amino radical is protected in the form of carbamate by a radical R=alkyloxycarbonyl.

The conversion of the nitro radical into an alkylamino radical is carried out by reductive alkylation when the radical Alk is a methyl or ethyl radical, or by reduction, formulation of the amine obtained and subsequent reduction of the formylamino radical when the radical Alk represents methyl.

The reductive alkylation is carried out by hydrogenation, under a pressure of hydrogen in the presence of Raney nickel, working in methanol at a temperature of between 20 and 40° C. and at a pressure of between 100 and 200 kPa.

The alkylation is carried out under hydrogen pressure by addition of benzaldehyde and then formaldehyde in the case where Alk is a methyl radical, or ethanal in the case where Alk is an ethyl radical.

The removal of the amino-protecting radical and the removal of the benzyl radical are carried out successively. When the amino-protecting radical is an acetyl radical, the removal is carried out by treatment in aqueous acid medium, in particular by hydrochloric acid. When Alk is a methyl or ethyl radical, the removal of the benzyl radical is carried out by hydrogenation under hydrogen in the presence of palladium-on-charcoal in aqueous acid medium, in particular aqueous hydrochloric acid, at a temperature of between 50 and 60° C. and at a pressure of between 100 and 200 kPa. In this case, the phenylalanine derivative of general formula (I) is obtained in salt form. It may optionally be released from its salt according to the usual methods which do not affect the rest of the molecule.

When it is desired to obtain a phenylalanine derivative of general formula (I) for which Alk is methyl by reduction and then formulation, the reduction of the nitro radical is carried out on 4-nitrophenylalanine of general formula (II) whose amine function is protected by a radical R and whose acid function has been protected beforehand, working in a reductive medium such as, for example, by treatment with zinc and ammonium chloride in a methanol/water mixture. The formulation of the amine obtained is carried out by formic acid, according to the usual methods for the reaction of an acid with an amine, which do not affect the rest of the molecule. In particular, the process is performed in tetrahydrofuran at a temperature of between 0 and 25° C. The reduction of the formylamino radical thus formed is advantageously carried out by boranes. For example, the process is performed using borane/methyl sulphide in tetrahydrofuran, at a temperature below 25° C.

The protection of the amine is carried out as described above. The protection of the carboxylic acid function is carried out according to the known methods which do not affect the rest of the molecule, in particular by esterification. The removal of the protecting radical from the amine and of the protecting radical from the acid are carried out simultaneously by treatment in aqueous acid medium, in particular by hydrochloric acid.

The product of general formula (I) may optionally be purified by physical methods such as crystallization or chromatography.

The product prepared according to the invention may either be obtained directly in salt form or may be converted into an addition salt with acids, into a metal salt or into an addition salt with nitrogen-containing bases, according to the methods known per se. These salts may be obtained, for example, by the action of a metal base (for example an alkali metal or alkaline-earth metal base), ammonia or an amine on a product according to the invention in a suitable solvent such as an alcohol, an ether or water, or by exchange reaction with a salt of an organic acid. The salt formed precipitates after optional concentration of its solution and it is separated out by filtration, settling or freeze-drying.

Examples of salts which may be mentioned are salts with alkali metals (sodium, potassium or lithium) or with alkaline-earth metals (magnesium or calcium), the ammonium salt, salts of nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine), as well as addition salts with inorganic acids (hydrochlorides, hydrobromides, sulphates, nitrates or phosphates) or with organic acids (succinates, fumarates, maleates, methanesulphonates, p-toluenesulphonates, isethionates, tartrates, acetates, propionates or citrates, or with substitution derivatives of these compounds).

The enantiomeric form of 2-amino-3-(4-alkylaminophenyl)propanoic acid thus prepared by the process according to the invention may be used in chemical synthesis. In particular, it may be used in the preparation of biologically active products and, more particularly, synergistic derivatives such as pristinamycin IB or the corresponding ethylamino derivative, the process being carried out starting with a strain of a microorganism which produces streptogramins, possessing at least one genetic modification which affects the biosynthesis of a precursor of the streptogramins from group B; the said mutant strain is cultured in a suitable culture medium, complemented with the product prepared according to the invention, by way of original precursor other than that whose biosynthesis is altered.

The strains used are strains which produce mutated, natural streptogramins (pristinamycin, virginiamycin, etc.). In particular, the mutant strains possess one or more genetic modifications in at least one of their genes involved in the biosynthesis of precursors of streptogramins from group B. This or these genetic modifications alter the expression of the said gene, that is to say make this gene and, where appropriate, another of the genes involved in the biosynthesis of the precursors, partially or totally incapable of coding for the natural enzyme involved in the biosynthesis of at least one precursor.

The examples which follow, which are given without any limitation being implied, illustrate the invention.

EXAMPLE 1

To a suspension of 200 g of (L)-phenylalanine in 1660 cm$^3$ of water at 20° C. are added, with stirring, 340 cm$^3$ of triethylamine. The mixture is kept stirring at a temperature in the region of 20° C. for 30 minutes until dissolution is complete, and is then cooled to 5° C. 126 cm$^3$ of acetic anhydride are added dropwise to this solution while maintaining an internal temperature in the region of 5° C. At the end of the addition, the mixture is maintained at 5° C. for one hour and then cooled to 0° C. 200 cm$^3$ of 36% hydrochloric acid solution are added dropwise to this solution while maintaining the temperature in the region of 0° C. At the end of the addition, the suspension is stirred for one hour at 0° C. and then filtered. The white precipitate obtained is rinsed with 400 cm$^3$ of water, drained and then dried under reduced pressure (20 kPa) at about 50° C.

227 g of (2S)-2-acetamido-3-phenylpropanoic acid are thus obtained in the form of a white solid melting at 160° C.

Preparation of (2S)-2-acetamido-3-(4-nitrophenyl) propanoic acid:

To a stirred solution of 32.0 g of (2S)-2-acetamido-3-phenylpropanoic acid in 46.1 cm$^3$ of 90% sulphuric acid cooled to −15° C. are added dropwise 6.4 cm$^3$ of 100% nitric acid, while maintaining the mixture at a temperature in the region of −15° C. At the end of the addition, the solution is maintained at −15° C. for an additional hour and is then warmed to 40° C., at which temperature 70.4 cm$^3$ of water are added. At the end of the addition of water, the solution is allowed to cool to a temperature in the region of 20° C. The precipitate obtained is filtered off, rinsed with twice 32 cm$^3$ of water, drained and then dried under reduced pressure (20 kPa) at about 50° C.

18.2 g of (2S)-2-acetamido-3-(4-nitrophenyl)-propanoic acid are thus obtained in the form of a white solid which decomposes at 191° C.

Preparation of (2S)-2-acetamido-3-(4-(N-methylbenzylamino)phenyl)propanoic acid dihydrochloride:

To 5.50 g of Raney nickel is added, at 20° C. with stirring, a solution of 5.00 g of (2S)-2-acetamido-3-(4-nitrophenyl) propanoic acid in 100 cm$^3$ of methanol. The solution thus obtained is flushed three times with nitrogen, then three times with hydrogen before being placed under a hydrogen pressure of 100 kPa with vigorous stirring at a temperature in the region of 30° C. for 2.5 hours. The solution is cooled to 25° C. and 2.90 cm$^3$ of benzaldehyde are added dropwise thereto. The mixture is kept stirring under a hydrogen pressure of 100 kPa for 2 hours and then 1.65 cm$^3$ of aqueous 35% formaldehyde solution are added thereto. The stirring under a hydrogen pressure is continued for a further 2 hours and the solution is then flushed with nitrogen, filtered through clarcel and then concentrated to dryness under reduced pressure (20 kPa) at a temperature in the region of 40° C.

6.06 g of (2S)-2-acetamido-3-( 4-(N-methylbenzylamino) phenyl)propanoic acid are thus obtained in the form of a beige solid which decomposes at 160° C.

Preparation of (2S)-2-amino-3-(4-(N-methylamino) phenyl)propanoic acid dihydrochloride:

To a suspension of 1.60 g of (2S)-2-acetamido-3-(4-(N-methylbenzylamino)phenyl)propanoic acid in 4.80 cm$^3$ of water at 20° C. are added, with stirring, 9.60 cm$^3$ of aqueous 36% hydrochloric acid solution. The solution thus obtained is maintained at reflux for 2.5 hours, cooled to 20° C. and then poured into a solution of 0.16 g of 5% palladium-on-charcoal in 1.60 cm$^3$ of water. The mixture thus obtained is flushed three times with nitrogen, then three times with hydrogen before being placed under a hydrogen pressure of 100 kPa, with vigorous stirring at a temperature in the region of 50° C. for 2 hours, then cooled to 20° C., filtered through clarcel, rinsed with twice 5.00 cm$^3$ of water and then concentrated to dryness under reduced pressure (20 kPa) at a temperature in the region of 40° C. 12.90 cm$^3$ of 2-propanol are added to the dry extract. The suspension thus obtained is maintained at reflux for 1 hour, cooled to a temperature in the region of 20° C., filtered, rinsed with 3.00 cm$^3$ of 2-propanol, drained and then dried under reduced pressure (20 kPa) at about 40° C.

1.11 g of (2S)-2-amino-3-(4-(N-methylamino)-phenyl) propanoic acid dihydrochloride are thus obtained in the form of a beige solid which decomposes at 208° C.

[ee=96.5% by liquid phase chromatography on a chiral stationary phase composed of a crown ether impregnated on silica (Crownpak CR®)].

EXAMPLE 2

Preparation of (2S)-2-amino-3-(4 nitrophenyl)-propanoic acid

To a stirred solution of 33.37 g of (L)-phenylalanine in 56.1 cm³ of 95% sulphuric acid cooled to −15° C. are added dropwise 9.95 cm³ of 100% nitric acid, while maintaining the mixture at a temperature in the region of −16° C. At the end of the addition, the solution is maintained at −16° C. for 2.5 hours, 250 cm³ of water are added dropwise thereto while allowing the solution to warm to a temperature in the region of −10° C., then about 180 cm³ of aqueous 30% sodium hydroxide solution are added dropwise thereto until the pH=4.70, while allowing the solution to return to a temperature in the region of 25° C. The precipitate obtained is filtered off, taken up in 350 cm³ of water, maintained at a temperature in the region of 50° C. for 0.5 hour, cooled to a temperature in the region of 20° C., filtered, drained and then dried under reduced pressure (20 kPa) at about 40° C.

24.35 g of (2S)-2-amino-3-(4-nitrophenyl)-propanoic acid are thus obtained in the form of a white solid which decomposes at 230° C.

Preparation of (2S)-2-acetamido-3-(4-nitrophenyl) propanoic acid:

To a suspension of 19.9 g of (2S)-2-amino-3-(4-nitrophenyl)propanoic acid in 78.6 cm³ of water at 20° C. are added, with stirring, 20.9 cm³ of aqueous 30% sodium hydroxide solution. The mixture is kept stirring at a temperature in the region of 20° C. for 30 minutes and is then cooled to 5° C. 13.7 cm³ of acetic anhydride are added dropwise to this solution while maintaining an internal temperature in the region of 5° C. At the end of the addition, the mixture is maintained at 5° C. for 0.25 hour and 9.5 cm³ of aqueous 30% sodium hydroxide solution are then added until dissolution is complete. To this solution are added dropwise 26.0 cm³ of 36% hydrochloric acid solution, while allowing the temperature to rise to 15° C. At the end of the addition, the suspension is stirred for 0.5 hour at 15° C., filtered, drained and then dried under reduced pressure (20 kPa) at about 40° C.

19.5 g of (2S)-2-acetamido-3-(4-nitrophenyl)-propanoic acid are thus obtained in the form of a white solid which decomposes at 191° C.

(2S)-2-Amino-3-[4-(N-methylamino)phenyl]-propanoic acid may be obtained from (2S)-2-acetamido-3-(4-nitrophenyl)propanoic acid, as described in Example 1.

EXAMPLE 3

Preparation of methyl (2S)-2-amino-3-(4-nitrophenyl) propanoate hydrochloride:

To a suspension of 177.4 g of (2S)-2-amino-3-(4-nitrophenyl)propanoic acid in 1800 cm³ of methanol at 0° C. are added dropwise, with stirring, 69.8 cm³ of thionyl chloride, while maintaining the temperature of the mixture between 0 and 10° C. At the end of the addition, the mixture is maintained at reflux for 6 hours. 900 cm³ of 2-propanol and then 1600 cm³ of distilled methanol are then added to the mixture at reflux. The suspension thus obtained is cooled to room temperature, maintained for one hour at room temperature with stirring, filtered, rinsed with 180 cm³ of 2-propanol, drained and then dried under reduced pressure (20 kPa) at about 40° C.

188.1 g of methyl (2S)-2-amino-3-(4-nitrophenyl) propanoate hydrochloride are thus obtained in the form of a white solid which melts at 218° C.

Preparation of methyl (2S)-2-ethanamido-3-(4--nitrophenyl)propanoate:

To a suspension of 186.1 g of methyl (2S)-2-amino-3-(4-nitrophenyl)propanoate hydrochloride in 930 cm³ of tetrahydrofuran at 20° C. with stirring are added 83 cm³ of acetic anhydride. The mixture is cooled to 5° C. and 241 cm³ of triethylamine are then added dropwise such that the temperature of the reaction mixture is kept below 20° C. At the end of the addition, the mixture is kept stirring at 20° C. for one hour and then cooled to 5° C. 460 cm³ of water are added at 5° C. The mixture is returned to 20° C., stirred for 30 minutes at this temperature and then separated by settling of the phases. The lower aqueous phase is removed and the upper organic phase is poured onto 2300 cm³ of water at 20° C. The mixture is brought to reflux and 600 cm³ of tetrahydrofuran are distilled off. The suspension obtained is cooled to 20° C. with stirring, filtered, rinsed three times with 200 cm³ of water, drained and then dried under reduced pressure (20 kPa) at about 50° C.

171.2 g of methyl (2S)-2-ethanamido-3-(4-nitrophenyl) propanoate are thus obtained in the form of a white cottony solid which melts at 126° C.

Preparation of methyl (2S)-3-(4-aminophenyl)-2-ethanamidopropanoate:

To a suspension of 170.0 g of methyl (2S)-2-ethanamido-3-(4-nitrophenyl)propanoate, 417.5 g of zinc powder and 850 cm³ of methanol at 10° C., with stirring, is added a solution of 341.6 g of ammonium chloride in 850 cm³ of water such that the temperature of the mixture is kept below 25° C. At 25° C., the suspension is filtered, rinsed with 850 cm³ of methanol and then rinsed with 450 cm³ of water. The filtrate and the two washings are combined, brought to reflux in order to fractionally distill off all of the methanol, and the mixture is then cooled to room temperature. 2000 cm³ of dichloromethane are added at 20° C. The mixture is stirred at 20° C. for 30 minutes and then separated by settling of the phases. The lower organic phase is removed and dried over anhydrous sodium sulphate. After filtration of the sodium sulphate, the solution is concentrated at 30° C. under reduced pressure (20 kPa) and then dried under reduced pressure (20 kPa) at about 25° C.

123.4 g of methyl (2S)-3-(4-aminophenyl)-2-ethanamidopropanoate are thus obtained in the form of a yellow solid which melts at 141° C.

Preparation of methyl (2S)-2-ethanamido-3-(4-methanamidophenyl)propanoate:

To 158 cm³ of acetic anhydride at 0° C. are added dropwise, with stirring, 76.7 cm³ of formic acid. The solution is then heated at 50° C. for 2 hours and then cooled to 0° C., at which temperature 150 cm³ of tetrahydrofuran are added. A solution of 148.6 g of methyl (2S)-3-(4-aminophenyl)-2-ethanamidopropanoate in 1500 cm³ of tetrahydrofuran is added to this mixture such that the temperature of the reaction mixture is maintained below 10° C. At the end of the addition, the mixture is allowed to return to 25° C. and 1500 cm³ of water are then added. The mixture is brought to reflux, the tetrahydrofuran is fractionally distilled off and the mixture is then cooled to 25° C. and maintained at this temperature for 3 hours. The suspension obtained is filtered, rinsed with 150 cm³ of water, drained and dried under reduced pressure (20 kPa) at 40° C.

123.5 g of methyl (2S)-2-ethanamido-3-(4-methanamidophenyl)propanoate are thus obtained in the form of a beige solid which melts at 126° C.

Preparation of methyl (2S)-2-ethanamido-3-[4-(N-methylamino)phenyl]propanoate:

To a solution of 100.0 g of methyl (2S)-2-ethanamido-3-(4-methanamidophenyl)propanoate in 3000 cm³ of tetrahydrofuran at 20° C. with stirring are added, under nitrogen, 378 cm³ of a 2 M solution of borane/methyl sulphide in tetrahydrofuran such that the temperature of the reaction mixture is maintained below 25° C. At the end of the addition, the reaction mixture is kept stirring for 1 hour at 25° C. and 1000 cm³ of methanol are then added dropwise. At the end of the addition of the methanol, the mixture is stirred at 25° C. under nitrogen for 16 hours and then concentrated under reduced pressure (20 kPa) at a temperature of 40° C. At the end of the concentration, the mixture is allowed to return to 25° C. under nitrogen and 1000 cm³ of dichloromethane and 1000 cm³ of saturated aqueous sodium chloride solution are then added. The mixture is stirred for 30 minutes at 25° C. and is then separated by settling of the phases. The lower organic phase is removed and dried over anhydrous sodium sulphate. After filtration of the sodium sulphate, the solution is concentrated at 30° C. under reduced pressure (20 kPa).

95.1 g of methyl (2S)-2-ethanamido-3-(4-N-methylaminophenyl)propanoate are thus obtained in the form of a white solid which melts at 151° C.

Preparation of (2S)-2-amino-3-(4-(N-methylamino)phenyl)propanoic acid dihydrochloride:

A solution of 95.0 g of methyl (2S)-2-ethanamido-3-(4-N-methylaminophenyl)propanoate in 285 cm³ of water and 570 cm³ of 36% hydrochloric acid is maintained at reflux for 5 hours and then concentrated. To the concentrated mixture, cooled to 80° C., are added 900 cm³ of 2-propanol. The suspension obtained is maintained at 80° C. for 2 hours and then cooled to room temperature. The precipitate is filtered off, rinsed twice with 200 cm³ of 2-propanol, drained and then dried under reduced pressure (20 kPa) at about 40° C.

77.5 g of (2S)-2-amino-3-(4-(N-methylamino)phenyl)propanoic acid dihydrochloride are thus obtained in the form of a white solid which melts at 210° C.

Use of 2-amino-3-(4-(N-methylamino)phenyl)propanoic acid

Preparation of pristinamycin $I_B$ [4-methylamino-de(4-dimethylamino)pristinamycin $I_A$]

A culture of the strain SP92::pVRC508 in production medium is prepared on a 60-conical-flask scale, as described below, with addition at 16 hours of 1 ml of a solution at a concentration of 10 g/l in water of (2S)-2-amino-3-(4-(N-methylamino)phenyl)-propanoic acid. After culturing for 40 hours, the 1.8 liters of broth from the 60 conical flasks are extracted with 2 volumes of a mixture of 66% phosphate buffer 100 mM pH 2.9 and 34% acetonitrile, then centrifuged. The supernatant is extracted with twice 0.5 volume of dichloromethane. The dichloromethylene phases are washed with water and then combined, dried over sodium sulphate and evaporated. The dry extract is taken up in 20 ml of dichloromethane and injected onto a column of silica (30 g) made up in dichloromethane and eluted successively with steps of from 0 to 10% methanol in dichloromethane. The fractions containing the pristinamycin $I_B$ are pooled and concentrated to dryness. The dry residue is taken up in 6 ml of a mixture of 65% water and 35% acetonitrile and is injected onto a Nucleosil 7μ C8 10×250 mm semi-preparative column (Macherey Nagel) eluted with a mixture of 65% phosphate buffer 100 mM pH 2.9 and 35% acetonitrile. The fractions containing the pristinamycin $I_B$ are pooled and extracted with one volume of dichloromethane. The organic phase is washed with water, dried over sodium sulphate and then concentrated to dryness. 52 mg of pristinamycin $I_B$ are obtained.

¹H NMR spectrum (400 MHz, CDCl₃, δ in ppm, ref. TMS): 0.71 (dd, J=16 and 6 Hz, 1H, 5 β₂); 0.92 (t, J=7.5 Hz, 3H: CH₃ 2 γ); from 1.10 to 1.40 (mt, 2H: 3 β₂ and 3 γ₂); 1.34 (d, J=7.5 Hz, 3H: CH₃ 1 γ); from 1.50 to 1.85 (mt, 3H: 3 γ₁ and CH₂ 2 β); 2.03 (mt, 1H, 3 β₁); 2.22 (mt, 1H, 5 δ₂); 2.33 (broad d, J=16 Hz, 1H: 5 δ₁); 2.40 (d, J=16 Hz, 1H: 5 β₁); 2.82 (mt, 1H: 5 ε₂); 2.81 (s, 3H: 4 NCH₃ para on the phenyl); 2.90 (dd, J=12 and 4 Hz, 1H: 4 β₂); 3.29 (s, 3H: 4 NCH₃); from 3.20 to 3.45 and 3.60 (2 mts, 1H each: CH₂ 3 δ); 3.40 (t, J=12 Hz, 1H: 4 β₁); 4.57 (dd, J=7 and 8 Hz, 1H, 3 α); 4.75 (broad dd, J=13 and 7 Hz, 1H: 5 ε₁); 4.83 (mt, 1H: 2α), 4.89 (broad d, J=10 Hz, 1H: 1α); 5.24 (dd, J=12 and 4 Hz, 1H: 4 α); 5.32 (broad d, J=6 Hz, 1H: 5 α); 5.89 (d, J=9 Hz, 1H: 6 α); 5.90 (broad q, J=7.5 Hz, 1H: 1β); 6.53 (d, J=9 Hz, 1H: NH 2); 6.53 (d, J=8 Hz, 2H: 4ε); 7.03 (d, J=8 Hz, 2H: 4δ); from 7.10 to 7.35 (mt, 5H: 6 aromatic H); 7.46 (mt, 2H: 1' H₅ and 1' H₄); 7.85 (dd, J=5.5 and 2 Hz, 1H: 1' H₆); 8.44 (d, J=10 Hz, 1H: NH 1); 8.76 (d, J=9 Hz, 1H: NH 6); 11.63 (s, 1H: OH).

Culturing of the strain SP92::PVRC508

The mutant SP92::pVRC508 was cultured in liquid production medium. The fermentation was carried out as follows: 0.5 ml of a suspension of spores from the abovementioned strain is added under sterile conditions to 40 ml of inoculum medium in a 300 ml conical flask containing baffle plates. The inoculum medium consists of 10 g/l of Corn Steep, 15 g/l of sucrose, 10 g/l of (NH₄)₂SO₄, 1 g/l of K₂HPO₄, 3 g/l of NaCl, 0.2 g/l of MgSO₄.7H₂O and 1.25 g/l of CaCO₃. The pH is adjusted to 6.9 with sodium hydroxide and calcium carbonate is then introduced. The conical flasks are stirred for 44 hours at 27° C. on a rotary stirrer at a speed of 325 rpm. 2.5 ml of the above 44-hour-old culture are added, under sterile conditions, to 30 ml of production medium in a 300 ml conical flask. The production medium consists of 25 g/l of soya flour, 7.5 g/l of starch, 22.5 g/l of glucose, 3.5 g/l of feeding yeast, 0.5 g/l of zinc sulphate and 6 g/l of calcium carbonate. The pH is adjusted to 6.0 with hydrochloric acid and the calcium carbonate is then introduced. The flasks are stirred at 27° C. on a rotary stirrer at a speed of 325 rpm.

I claim:

1. A process for the preparation of an enantiomeric form of 2-amino-3-(4-alkylaminophenyl)propanoic acid of formula (I) or a salt thereof:

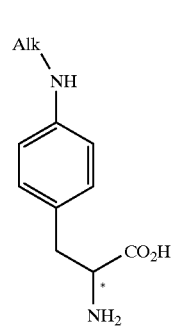

(I)

in which Alk represents an alkyl radical containing 1 to 2 carbon atoms, said process comprising:

nitrating (L)-phenylalanine or (D)-phenylalanine to obtain a nitro radical of 4-nitrophenylalanine of formula (II):

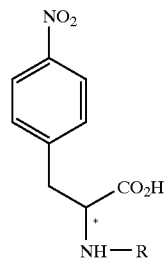

(II)

in which R is a hydrogen atom or a protecting radical, protecting, if R is H, the amine function of said (L)- or (D)-phenylalanine, and converting said nitro radical of formula (II) into an alkylamino radical, wherein when (L)-phenylalanine is used, the final product is the (S)-enantiomer of 2-amino-3-(4-alkylaminophenyl)propanoic acid, and when (D)-phenylalanine is used, the final product is the (R)-enantiomer of 2-amino-3-(4-alkylaminophenyl) propanoic acid.

* * * * *